United States Patent
Cogger

(10) Patent No.: US 6,524,287 B1
(45) Date of Patent: Feb. 25, 2003

(54) HOUSING APPARATUS WITH REAR ACTIVATED RETURN BUTTON FOR INSTILLING A MEDICATION INTO AN EYE

(75) Inventor: John J. Cogger, Irvine, CA (US)

(73) Assignee: Advanced Medical Optics, Santa Ana, CA (US)

( * ) Notice: Subject to any disclaimer, the term of this patent is extended or adjusted under 35 U.S.C. 154(b) by 226 days.

(21) Appl. No.: 09/685,523

(22) Filed: Oct. 10, 2000

(51) Int. Cl.$^7$ .............................................. A61M 35/00
(52) U.S. Cl. .................. 604/298; 604/289; 604/294
(58) Field of Search .................. 604/890.1, 294–302; 222/631, 160, 325, 322, 596, 321.8, 630, 167

(56) References Cited

U.S. PATENT DOCUMENTS

| 4,792,334 A | 12/1988 | Py | 604/301 |
| 4,908,024 A | 3/1990 | Py | 604/300 |
| 4,946,452 A | 8/1990 | Py | 604/301 |
| 4,981,479 A | 1/1991 | Py | 604/302 |
| 5,085,651 A | 2/1992 | Py | 604/298 |
| 5,133,702 A | 7/1992 | Py | 604/302 |
| 5,163,929 A | 11/1992 | Py | 604/298 |
| 5,267,986 A | 12/1993 | Py | 604/294 |
| 5,320,845 A | 6/1994 | Py | 424/427 |
| 5,401,259 A | 3/1995 | Py | 604/294 |
| 5,499,751 A | 3/1996 | Meyer | 222/386 |
| D368,774 S | 4/1996 | Py | D24/113 |
| D374,719 S | 10/1996 | Py | D24/120 |
| 5,613,957 A | 3/1997 | Py | 604/294 |
| 5,641,004 A | 6/1997 | Py | 141/3 |
| 5,685,869 A | 11/1997 | Py | 604/294 |
| 5,746,728 A | 5/1998 | Py | 604/298 |
| 5,855,322 A | 1/1999 | Py | 239/11 |

*Primary Examiner*—Dennis Ruhl
*Assistant Examiner*—Linh Truong
(74) *Attorney, Agent, or Firm*—Walter A. Hackler; Peter Jon Gluck

(57) ABSTRACT

Apparatus for instilling a medicament into an eye includes a housing, a reservoir, disposed in the housing and movable therein along a longitudinal axis, for containing a medicament and a nozzle disposed for instilling a dose of the medicament into an eye. An actuator is disposed between the reservoir and the nozzle for metering doses of medicament from the reservoir to the nozzle and forcing each metered dose through said nozzle upon acceleration of said actuator. A spring causes longitudinal displacement of the reservoir toward a housing rear upon release of the spring from a compressed state and a depressible button disposed at the housing rear that moves the reservoir in a forward direction toward a housing front to cause compression of said spring. A trigger, disposed in the housing releases the compressed spring and causes rearward movement of the reservoir.

18 Claims, 3 Drawing Sheets

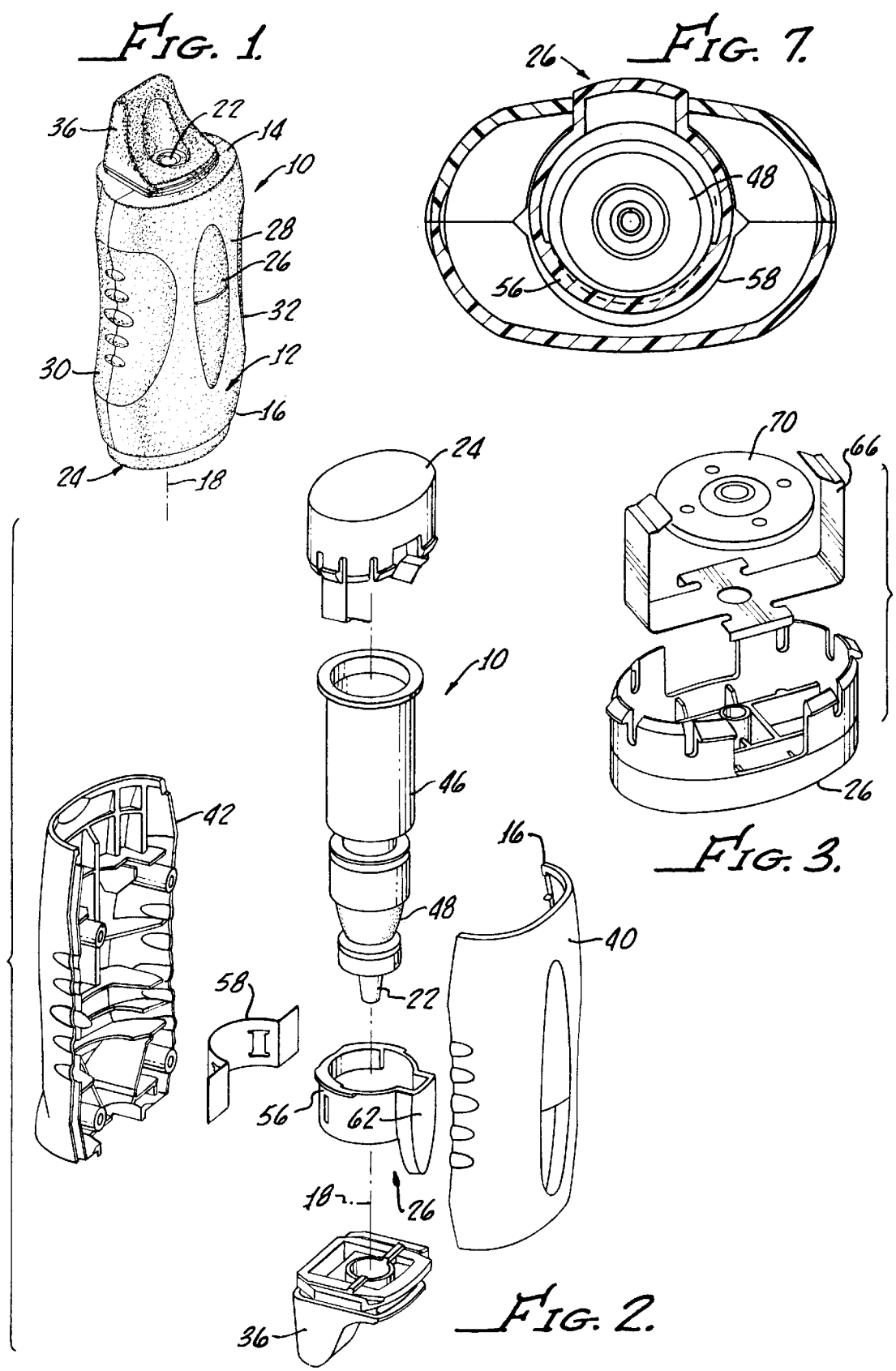

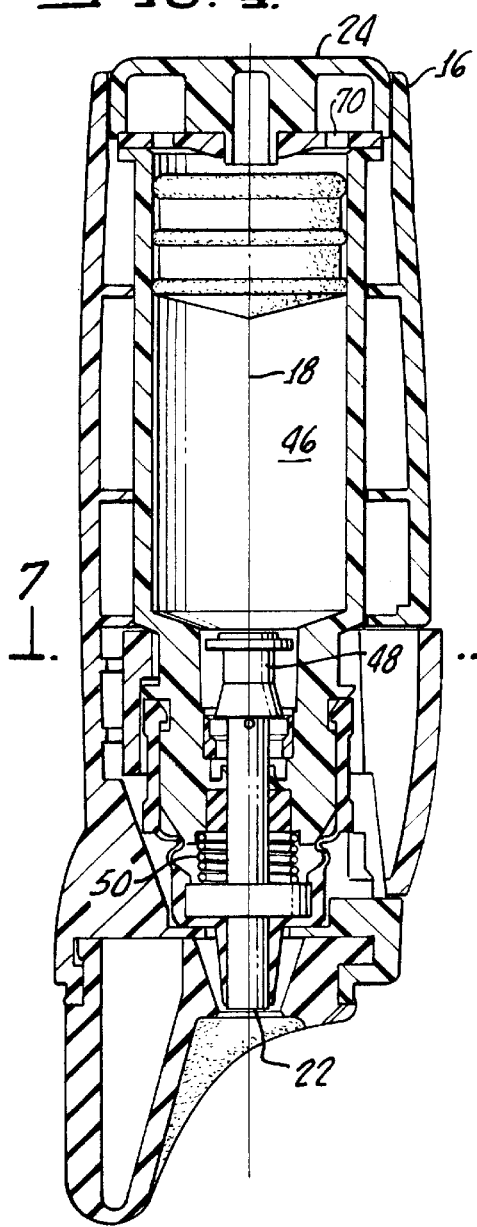
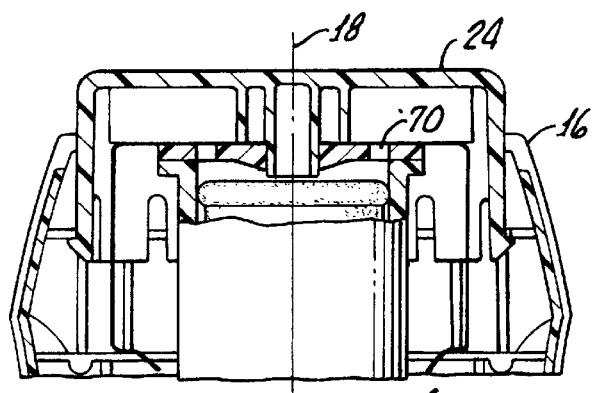
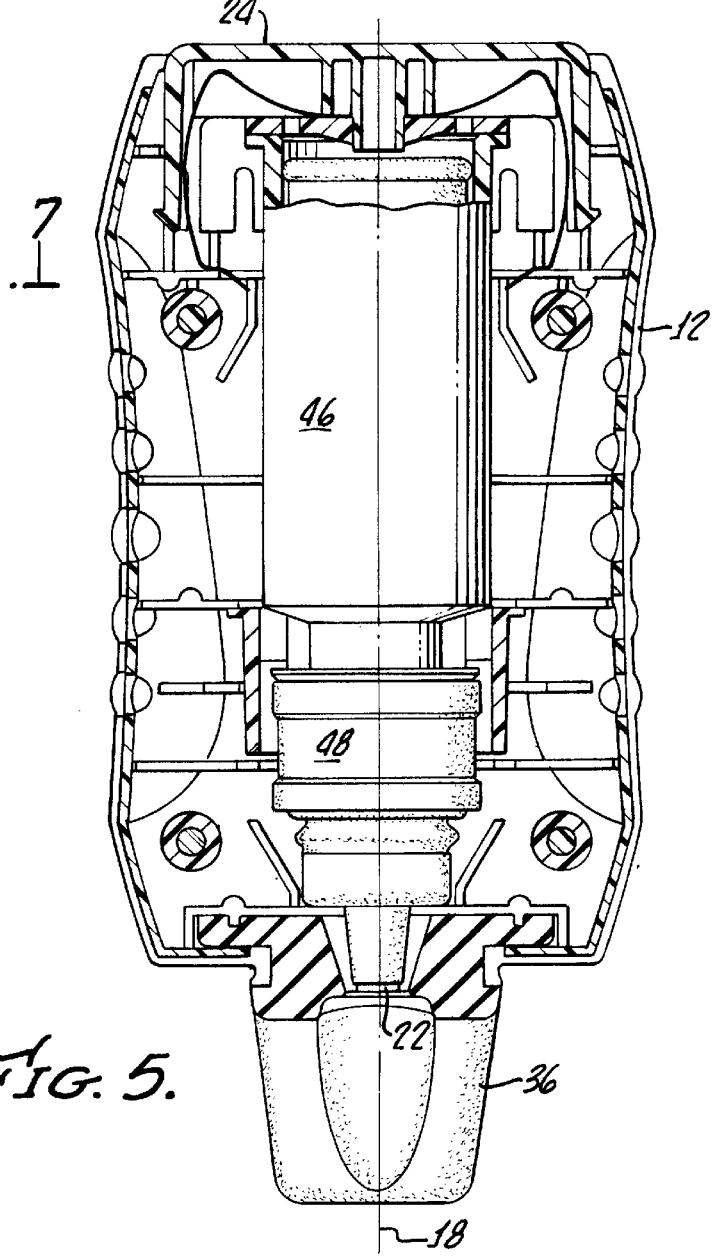

HOUSING APPARATUS WITH REAR ACTIVATED RETURN BUTTON FOR INSTILLING A MEDICATION INTO AN EYE

The present invention generally relates to apparatus for dispensing microliter amounts of medicament and is more particularly directed to apparatus for instilling a medicament into an eye.

A great number of devices have been developed for instilling medicament to an eye. Well know eye drop containers conventionally include a squeezable container and a nozzle for releasing drops of medicament into the eye by compression of the container. Obviously, this apparatus affords no practical method of dispensing a measured dose of medicament inasmuch as the liquid dispensed from the nozzle is dependent upon the amount of compression of the container. Thus, there is no way of accurately controlling the volume of each dose of medicament released into the eye and, further, the smallest drop obtainable is the result of the combined effective gravity and surface tension.

When preservative-free medicaments are utilized, simple eye drop dispensers are not practical because there are no means for preventing the tip from being contaminated due to its exposure to air. Such tip contamination ultimately spreads to the medicament in the container.

In an attempt to overcome these problems, apparatus has been developed for applying a medicament to an eye which includes a nozzle having a seam which is normally in a closed position for preventing the passage of medicament through the nozzle, and which opens in response to a flow of medicament of sufficient pressure to enable opening of the seam in order to permit the passage of medicament through the nozzle for release into the eye, see U.S. Pat. No. 5,685,869.

While this nozzle is suitable, there is difficulty in coupling the nozzle with a suitable reservoir of medicament in order to create a working, producible device for multiple dose delivery of a preservative-free product of sufficient dose accuracy for consumer benefit and regulatory body registration over an extended period of time of up to six months or more.

Operation of prior art devices such as set for the in the hereinabove referenced U.S. Patent typically cause a small negative pressure or vacuum within the medicament container during operation. When a collapsible container is utilized to accommodate shrinking of volume of the medicament reservoir, the materials of construction do not satisfactorily inhibit the permeating of air through the container walls to provide a desired long term use in storage of the device without compromise of the stored medicament.

U.S. patent application Ser. No. 09/435,703 filed Nov. 8, 1999 entitled MULTIPLE PRECISION DOSE PRESERVATIVE FREE MEDICATION DELIVERY SYSTEM provides a nozzle and medicament reservoir combination which enables multiple dose delivery of a preservative-free product with accurate dose dispensing over extended periods of time.

Such axial movement may be provided by a button disposed at a rear of a housing in order to compress a fluid reservoir and actuator together. The compressed condition is held by a latching mechanism and upon release of the latch, or trigger, the two parts are rapidly accelerated apart from each other in an opposite axial direction in the actuator or pump, produces a dose that is sprayed out of a nozzle.

The present invention provides for apparatus enabling axial compression of a spring and the housing for enabling the fluid reservoir to move backward when a trigger is released. The original motion to cock the system is delivered by a patient operated push button or cap at the back of the housing.

SUMMARY OF THE INVENTION

An apparatus for instilling a medicament into an eye generally includes a housing having a front and rear with a longitudinal axis therebetween. A reservoir for containing a medicament is provided and disposed in the housing and movable therein therealong the longitudinal axis.

A nozzle disposed proximate the housing front, is provided for instilling a dose of medicament to an eye and an actuator, or pump, disposed between the reservoir and the nozzle is provided for metering doses of medicament from the reservoir to the nozzle and forcing each metered dose through the nozzle upon actuation of the actuator.

A spring is provided for causing a longitudinal displacement of the reservoir toward the housing rear upon release of the spring from a compressed state, the longitudinal displacement causing actuation of the actuator. A depressible button is disposed at the housing rear for moving the reservoir in a forward direction toward the housing front to cause compression or cocking of the spring. A trigger disposed in the housing provide for the release of the compressed spring and causing rearward motion of the reservoir.

More particularly, the trigger may include a latch for holding the spring in the compressed state until depression of the trigger, and preferably the trigger is disposed on a side of the housing.

Importantly, a second spring may be provided and disposed within the housing for causing the depressible button to separate from the reservoir and move towards the housing rear after compression of the spring. This is important in that a comfortable operating position for a patient is often with his or her finger resting on the depressible button.

In order to produce a sufficient consistent dose, which is critical in most of the ophthalmic medication delivery applications, the reservoir must be free to move rearwardly during actuation. If a patient's finger is resting on the button and the button does not separate from the reservoir, interference with the operation may lead to suboptimal dosing and the risk of patient not receiving sufficient medication. Thus, the second spring enables the button to move independently and decouple, or separate, from the reservoir, thus enabling free movement of the reservoir despite continued contact by a patient with the button.

The present invention further includes apparatus for operating an eye drop dispenser with the eye drop dispenser including a reservoir containing a medicament, a nozzle for instilling a dose of the medicament into an eye and a spring driven actuator for metering doses of medicament from the reservoir to the nozzle and forcing each measured dose through the nozzle upon axial displacement between the actuator and the reservoir along a longitudinal axis. Specifically, this apparatus includes a housing for receiving the reservoir, nozzle and actuator in combination with a depressible button which is disposed at a rear of a housing for moving the reservoir in a forward directional towards a housing front to cause compression of the spring and a trigger disposed in the housing for releasing the compressed spring and causing the rearward motion of the reservoir.

BRIEF DESCRIPTION OF THE DRAWINGS

The advantages and features of the present invention will be better understood by the following description when considered in conjunction with the accompanying drawings in which:

FIG. 1 is a perspective view of apparatus in accordance with the present invention generally showing a housing, a nozzle, a depressible button disposed at the housing rear and a trigger disposed in a site of the housing;

FIG. 2 is an exploded view of the apparatus showing FIG. 1 more clearly showing a reservoir for containing a medicament and an actuator, or pump, disposed between the reservoir and the nozzle;

FIG. 3 is a cross-sectional view of the apparatus showing the button being depressed for moving the reservoir in a forward direction within the housing;

FIG. 4 is an exploded perspective view of the compressible button in accordance with the present invention;

FIG. 5 is a cross-sectional view of the apparatus showing FIG. 1 taking along a perpendicular axis;

FIG. 6 is a partial cross-sectional view showing a button being separated or decoupled from the reservoir by a release spring;

FIG. 7 is a cross-sectional view taken along the line 7—7 of FIG. 3, more clearly showing a cross-sectional view the trigger of the present invention;

DETAILED DESCRIPTION

Figure 8:
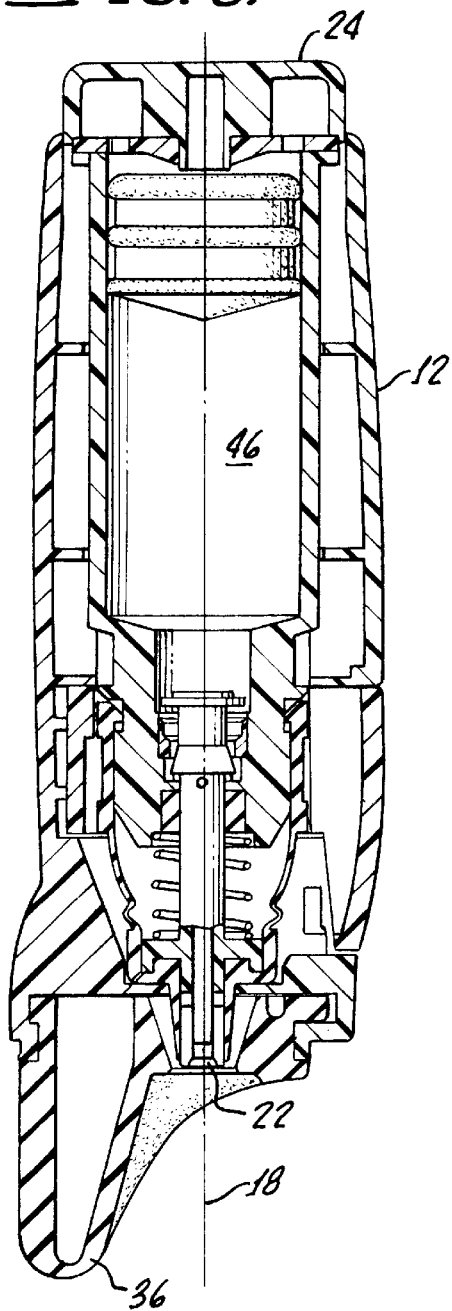
FIG. 8 is a cross-section view similar to FIG. 4 in which the reservoir has been released and moved rearwardly toward the button for dispensing a dose of medicament through a nozzle.

With reference to FIG. 1, there is shown apparatus 10 for instilling a medicament into an eye (not shown) which includes a housing 12 having a front 14 and a rear 16 with a longitudinal axis 18 therebetween. Also shown is a nozzle 22 disposed proximate the housing front 14 for instilling a dose of medicament (not shown) into an eye (not shown), a depressible button 24 disposed at the housing rear 16 and a trigger 26 disposed in a side 28 of the housing 12.

All of the components of the apparatus 10 may be formed from conventional materials suitable for use with dispensing medication for eyes. The housing 12 may include contoured surfaces 30, 32 for facilitation handling of the housing 12 and a support 36 may be provided in order to steady the nozzle 22 at a fixed distance from a patient's eye (not shown).

As shown in FIG. 2, the housing 12 may include two separate conforming shells 40, 42 to both facilitating manufacture of the housing 12 and assembly of the apparatus 10.

A reservoir 46, for containing a medicament, is disposed within the housing 12 and movable therein along the longitudinal axis 18 and an actuator 48, disposed between the reservoir 46 and the nozzle 22, is provided for metering doses of the medicament from the reservoir 46 to the nozzle 22 and forcing the medicament though the nozzle 22 upon actuation of the actuator.

The actuator 48, chamber 46 and nozzle 22 are fully described in U.S. patent application Ser. No. 09/435,703 entitled MULTIPLE PRECISION DOSE, PRESERVATIVE FREE MEDICATION DELIVERY SYSTEM and filed Nov. 8, 1999. This application is incorporated herewith in its entirety, including both specification and drawings, by this specific reference thereto for the purpose of describing the nozzle 22 actuator 48 and reservoir 46 as well as the operation thereof.

As described in the referenced patent application, a spring 50, shown in a compressed state in FIG. 3, causes longitudinal displacement of the reservoir 46 toward the housing rear 16 upon release of the spring 50 from a compressed state, the longitudinal displacement causing actuation of the actuator as described in the referenced patent application.

Figure 9:
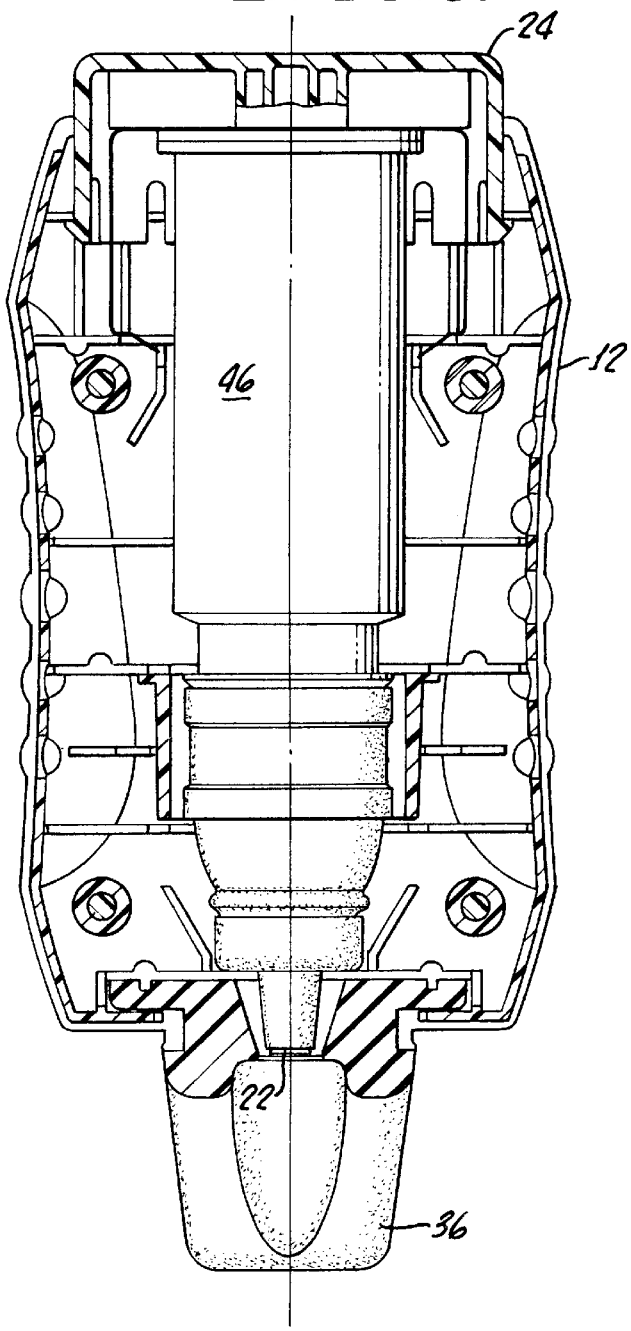
FIG. 9 is a cross-sectional view similar to FIG. 5 showing a reservoir in a rear position against the button after release of the compressed spring by the trigger.

As shown in FIGS. 1–6 and 8–9, the button 24 when depressed, as shown in FIGS. 3 and 5, causes forward movement of the reservoir 46 and a "cocking" or compression of the spring 50. The trigger 26 includes a latch 56 for engaging the actuator 48 in order to hold the spring 50 in a compressed state with the latch being held in position by a latch spring 58 as shown in cross-sectional view in FIG. 7.

Depression of trigger tab 62 releases the spring 50 from its compressed state by disengaging the trigger latch 56 from the actuator 48. This causes rearward motion of the reservoir 46 and a metering of a dose of medicament from the reservoir 46 to and through the nozzle 22 as hereinabove described.

Thus, in operation, the button 24 is pushed to move the reservoir 46 in a forward direction to compress the spring 50 as shown in FIGS. 3 and 5. Upon release of the button 24, a leaf spring 66 causes the button 24 to separate, or decouple, from the reservoir and move toward the housing rear 16. As a result, the button 24 after depressing the reservoir 46 is not accelerated by the spring 50 upon release by the trigger 26. Accordingly, its mass does not load the spring 50, and this serves to alleviate the load on the spring 50 which makes it more efficient and therefore apparatus 10 becomes more reliable and capable of producing consistent and reliable metered doses of medicament.

The button 24 protrudes from the housing rear in order to provide users access thereto. Decoupling of the button 24 of the reservoir 46 is of further importance in order to provide sufficient and consistent metering of doses. The button 24 must be free to retract unencumbered. This is necessitated by patient usage. Typically, if a patient's finger is resting on the button when operating the apparatus 10, such contact can interfere with the dosing accuracy because of interference of the rearward motion of the reservoir 46 during the actuation. Decoupling of the button 24 from the reservoir 46 after cocking the actuation 46 to compress the spring 50, enables subsequent touching of the button 24 without interference in operation of the actuator.

Upon release of the reservoir 46, its rearward motion causes it to reengage the button 24. A damper 70, most clearly shown in FIG. 4, is disposed between the reservoir 46 and the button 24, causes the deceleration of the reservoir 46 in order to reduce impact force between the reservoir 46 and the button 24 which minimizes stress on the apparatus components and to reduce noise during operation of the apparatus 10.

Although there has been hereinabove described apparatus for instilling medicament into an eye in accordance with the present invention, for the purpose of illustrating the manner in which the invention may be used to advantage, it will be appreciated that the invention is not limited thereto. Accordingly, any and all modifications, variations or equivalent arrangement which may occur to those skilled in the art should be considered to be within the scope of the invention as defined in the appended claims.

What is claimed is:

1. Apparatus for instilling a medicament into an eye, said apparatus comprising:

a housing having a front and a rear with a longitudinal axis therebetween;

a reservoir, disposed in said housing and movable therein along the longitudinal axis, for containing a medicament;

a nozzle disposed proximate the housing front for instilling a dose of the medicament into an eye;

an actuator disposed between said reservoir and said nozzle for metering doses of medicament from said reservoir to said nozzle and forcing each metered dose through said nozzle upon acceleration of said actuator;

a spring for causing longitudinal displacement of said reservoir toward the housing rear upon release of said spring from a compressed state, said longitudinal displacement causing actuation of said actuator;

a depressible button disposed at the housing rear for moving said reservoir in a forward direction toward the housing front to cause compression of said spring; and a trigger, disposed in said housing for releasing the compressed spring and causing rearward movement of said reservoir.

2. The apparatus according to claim 1 wherein said trigger includes a latch for molding said spring in the compressed state until depression of said trigger.

3. The apparatus according to claim 2 wherein said trigger is disposed on a side of said housing.

4. The actuator according to claim 3 further comprising a second spring, disposed within said housing for causing said depressible button to separate from said reservoir and move toward the housing rear after compressing the spring.

5. The apparatus according to claim 4 wherein said second spring comprises a leaf spring.

6. The apparatus according to claim 5 further comprising a damper disposed between said reservoir and said depressible button for decelerating the reservoir in order to reduce impact force between said reservoir and button and noise of such impact.

7. The apparatus according to claim 2 further comprising a second spring for causing said depressible button to decouple from said reservoir after compressing the spring in order to prevent acceleration of the button by the spring upon release by said trigger.

8. The apparatus according to claim 7 wherein said second spring comprises a leaf spring.

9. The apparatus according to claim 8 further comprising a damper, disposed between said reservoir and said button for decelerating the reservoir in order to reduce impact force between said reservoir and button and noise from such impact.

10. Apparatus for operating an eye drop dispenser, said eye drop dispenser including a reservoir for containing a medicament, a nozzle for instilling a dose of the medicament into an eye and a spring driven actuator for metering doses of medicament from said reservoir to said nozzle and forcing each metered dose through said nozzle upon axial displacement between said actuator and said reservoir along a longitudinal axis, said apparatus comprising:

a depressible button, disposed at a rear of said housing, for moving said reservoir in a forward direction toward a housing front to cause compression of said spring; and a trigger, disposed in said housing, for releasing the compressed spring and causing rearward movement of said reservoir.

11. The apparatus according to claim 10 wherein said trigger includes a latch for holding said spring in the compressed state until depression of said trigger.

12. The apparatus according to claim 11 wherein said trigger is disposed on a side of said housing.

13. The apparatus according to claim 12 further comprising a second spring disposed within said housing for causing said depressible button to separate from said reservoir to move toward the housing rear after compressing the spring.

14. The apparatus according to claim 13 wherein said second spring comprises a leaf spring.

15. The apparatus according to claim 14 further compressing a damper disposed between said reservoir and said depressible button for decelerating the reservoir in order to reduce impact force between said reservoir and button and noise of such impact.

16. The apparatus according to claim 11 further comprising a second spring for causing said depressible button to decouple from said reservoir after compressing the spring in order to prevent acceleration of the button by the spring upon release by said trigger.

17. The apparatus according to claim 16 wherein said second spring comprises a leaf spring.

18. The apparatus according to claim 17 further comprising a damper, disposed between said reservoir and said button for deceleration of the reservoir in order to reduce impact force between said reservoir and to reduce button and noise from such impact.

* * * * *